(12) United States Patent
Lui et al.

(10) Patent No.: US 8,637,673 B2
(45) Date of Patent: *Jan. 28, 2014

(54) METHOD FOR PRODUCING 2,2-DIFLUOROETHYLAMINE DERIVATIVES BY IMINE HYDROGENATION

(75) Inventors: Norbert Lui, Odenthal (DE); Stefan Antons, Leverkusen (DE)

(73) Assignee: Bayer Cropscience AG, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/256,590

(22) PCT Filed: Mar. 8, 2010

(86) PCT No.: PCT/EP2010/001419
§ 371 (c)(1),
(2), (4) Date: Oct. 6, 2011

(87) PCT Pub. No.: WO2010/105747
PCT Pub. Date: Sep. 23, 2010

(65) Prior Publication Data
US 2012/0022264 A1  Jan. 26, 2012

(30) Foreign Application Priority Data

Mar. 16, 2009  (EP) .................................. 09155209

(51) Int. Cl.
*C07D 213/53* (2006.01)
(52) U.S. Cl.
USPC ............................ 546/329; 544/224; 548/146
(58) Field of Classification Search
None
See application file for complete search history.

(56) References Cited

U.S. PATENT DOCUMENTS

| | | | |
|---|---|---|---|
| 8,324,393 B2 * | 12/2012 | Lui et al. | 546/329 |
| 2008/0282953 A1 | 11/2008 | Joe | |
| 2009/0253749 A1 | 10/2009 | Jeschke et al. | |
| 2010/0048646 A1 | 2/2010 | Jeschke et al. | |
| 2010/0240705 A1 | 9/2010 | Jeschke et al. | |
| 2010/0274021 A1 | 10/2010 | Lui et al. | |

FOREIGN PATENT DOCUMENTS

| | | |
|---|---|---|
| DE | 102004047922 | 4/2006 |
| DE | 102006015467 | 10/2007 |
| EP | 2039684 | 9/2007 |
| WO | 2007/115644 | 10/2007 |
| WO | 2007/115646 | 10/2007 |
| WO | 2008/009360 | 1/2008 |
| WO | 2009/036901 | 3/2009 |

OTHER PUBLICATIONS

Harada, "Hydrogenation Reactions," The Chemistry of the Carbon-Nitrogen Double Bond, pp. 276-293, Jan. 1970.

(Continued)

*Primary Examiner* — Zinna Northington Davis
(74) *Attorney, Agent, or Firm* — Miles & Stockbridge P.C.

(57) ABSTRACT

Process for preparing 2,2-difluoroethylamine derivatives, wherein compounds of the general formula (IV) are hydrogenated to the corresponding 2,2-difluoroethylamine derivatives of the general formula (III), where the A, $R^1$ and $R^2$ radicals are each as defined in the description:

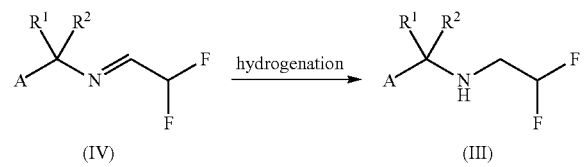

(IV)    (III)

3 Claims, No Drawings

(56) References Cited

OTHER PUBLICATIONS

Takagi et al., "Facile Preparation of Polyfluoroalkylated Aldimines From Polyfluoroalkanoic Acids," Synthesis, No. 11, pp. 1624-1628, (2007).

McBee et al., "Lithium Aluminum Hydride Reduction of Dufluoroacetic Acid," Proceeding of the Indian Academy of Science, vol. 64, pp. 108-110, (1954/55).

Kaneko et al., "A Remarkably Simple Route to Versatile Difluoromethylated Molecules," Journal of Org. Chem, vol. 58, pp. 2302-2312, (1993).

Brandwood et al., "Polyfluoro Diethyl and Ethyl Methyl Ethers: Their Preparation Using Cobalt (III) Fluoride and Potassium Tetrafluorocobaltate (III) and Their Dehydrofluorination," Journal of Fluorine Chemistry, vol. 5, pp. 521-535, (1975).

Lewis et al., "Difluorinated Carbaacyclonucleosides: Synthesis and Evaluation of Antiviral Activity," Journal of Chem. Res., vol. 8, pp. 844-ff, (2001).

"Reductive Alkylation-Preparation of Amines," Academic Press, pp. 291-303, (1967).

De Bievre et al., "Studies on Halogenated Alphiatic Compounds," Bull. Soc. Chim. Belg., vol. 68, pp. 401-408, fig. 3, (1959).

International Search Report for PCT/EP2010/001419 Mailed April 15, 2010.

European Search Report for EP-09 15 5209 Completed August 3, 2009.

\* cited by examiner

METHOD FOR PRODUCING 2,2-DIFLUOROETHYLAMINE DERIVATIVES BY IMINE HYDROGENATION

CROSS REFERENCE TO RELATED APPLICATIONS

This application is a §371, National Stage Application of PCT/EP2010/001419, filed Mar. 8, 2010, which claims priority to European Application No. 09155209.1, filed Mar. 16, 2009.

BACKGROUND OF THE INVENTION

1. Field of the Invention

The present invention relates to a process for preparing 2,2-difluoroethylamine derivatives proceeding from 2,2-difluoroethylimine derivatives. The present invention further provides the 2,2-difluoroethylimine derivatives used as starting compounds in this process according to the invention, the preparation thereof and the use thereof for preparing 2,2-difluoroethylamine derivatives.

2. Description of Related Art

Derivatives of 2,2-difluoroethylamines are important intermediates for preparing active agrochemical ingredients. Appropriate 2,2-difluoroethylamine derivatives can be used, for example, as insecticidally active enaminocarbonyl compounds, for example of 4-aminobut-2-enolide compounds. Enaminocarbonyl compounds which contain 2,2-difluoroethylamino units are known, for example, from WO 2007/115644, and WO 2007/115646.

WO 2007/115644, discloses that 2,2-difluoroethylamine derivatives, for example the compound of the formula (IIIa) below, can be prepared by alkylating the amine of the formula (Ia) with optionally substituted chloromethylpyridine of the formula (IIa) (scheme 1, of WO 2007/115644; cf. preparation of starting compounds; compounds of the formula (III); III-1:, N-[(6-chloropyridin-3-yl)methyl]-2,2-difluoroethyl-1-amine)

Scheme 1:

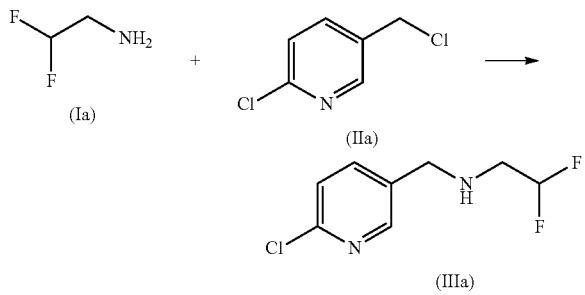

A disadvantage in this process is the low yield of 53%, which is caused by the possible polyalkylation of the amine nitrogen atom. This proportion of polyalkylation can only be reduced through the use of a large excess of amine, which is, though, uneconomic in the case of a costly amine.

WO 2009/036901, which claims the priority of European Patent Application No. 07116641, discloses that difluoroethylimines of the general formula IVa can be hydrogenated to difluoroethylamines of the general formula Va.

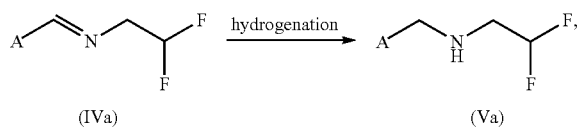

where A is:
pyrid-2-yl or pyrid-4-yl, or pyrid-3-yl which is optionally 6-substituted by fluorine, chlorine, bromine, methyl, trifluoromethyl or trifluoromethoxy, or pyridazin-3-yl which is optionally 6-substituted by chlorine or methyl, or pyrazin-3-yl, or 2-chloropyrazin-5-yl, or 1,3-thiazol-5-yl which is optionally 2-substituted by chlorine or methyl, or, is
pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or is

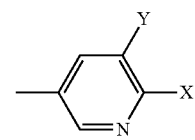

in which
X is halogen, alkyl or haloalkyl and
Y is halogen, alkyl, haloalkyl, haloalkoxy, azido or cyano.

SUMMARY OF THE INVENTION

Proceeding from the prior art cited, it is an object of the present invention to provide an alternative process for preparing 2,2-difluoroethylamine derivatives, which is preferably simple and inexpensive to perform. The 2,2-difluoroethylamine derivatives obtainable by this desired process should preferably be obtained with high yield and high purity. More particularly, the desired process should enable the desired target compounds to be obtained without the need for complex purification methods.

This object is achieved by a novel process for preparing 2,2-difluoroethylamine derivatives.

The process according to the invention is characterized in that 2,2-difluoroethylimine derivatives of the general formula (IV) are hydrogenated to the corresponding target compounds of the general formula (III) according to the following scheme 2:

Scheme 2:

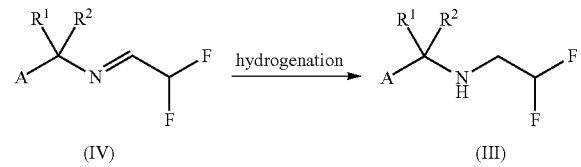

where the A radical is:
pyrid-2-yl or pyrid-4-yl, or pyrid-3-yl which is optionally 6-substituted by fluorine, chlorine, bromine, methyl, trifluoromethyl or trifluoromethoxy, or pyridazin-3-yl which is optionally 6-substituted by chlorine or methyl, or pyrazin-3-yl, or 2-chloropyrazin-5-yl, or 1,3-thiazol-5-yl which is optionally 2-substituted by chlorine or methyl, or is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or is

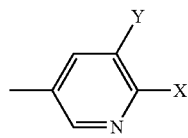

in which
X is halogen, alkyl or haloalkyl and
Y is halogen, alkyl, haloalkyl, haloalkoxy, azido or cyano.

DETAILED DESCRIPTION OF A PREFERRED EMBODIMENT

Preferred, particularly preferred and very particularly preferred definitions of the A radical shown in the abovementioned general formulae (III) and (IV) are elucidated below.
A is preferably selected from the group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.
A is more preferably selected from the group consisting of 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.
A is most preferably selected from the group consisting of 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.
In the abovementioned general formulae (III) and (IV), the $R^1$, and $R^2$, radicals are each defined as follows: $R^1$, and $R^2$, are each independently H or $C_1$-$C_6$-alkyl. $R^1$, and $R^2$, are more preferably each independently H or $C_1$-$C_3$-alkyl. $R^1$, and $R^2$, are most preferably each hydrogen.
The invention thus envisages that the desired 2,2-difluoroethylamine derivatives of the general formula (III) are prepared by a hydrogenation of the corresponding 2,2-difluoroethylimine derivatives of the general formula (IV). The desired 2,2-difluoroethylamine derivatives of the general formula (III) are obtained under the inventive reaction conditions and preferred reaction conditions specified in detail below with good yields in high purity, as a result of which the process according to the invention overcomes the abovementioned disadvantages. The desired compounds are obtained in a purity which generally does not necessitate an extensive workup of the direct reaction product. Compared to the process known from the prior art, which proceeds from an amine to be alkylated according to scheme 1, the yields can be improved by the process according to the invention. Furthermore, the purity achieved of the desired target compound by the process according to the invention is greater, since no polyalkylation takes place.

In the context of the present invention, the term "derivative" refers to a similar structure derived from the organic base structure (unit) in question, i.e. a 2,2-difluoroethylamine derivative is understood to mean, for example, a compound which includes a 2,2-difluoroethylamine unit.

The term "alkyl", either alone or in combination with further terms, for example haloalkyl, is understood in the context of the present invention to mean a radical of a saturated, aliphatic hydrocarbon group having 1, to 12, carbon atoms, which may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, $C_1$-$C_6$-alkyl radicals are particularly preferred. $C_1$-$C_4$-alkyl radicals are especially preferred.

According to the invention, the term "aryl" is understood to mean an aromatic radical having 6, to 14, carbon atoms, preferably phenyl.

The term "arylalkyl" is understood to mean a combination of "aryl" and "alkyl" radicals defined in accordance with the invention, the radical generally being bonded via the alkyl group; examples thereof are benzyl, phenylethyl or α-methylbenzyl, particular preference being given to benzyl.

In the context of the present invention, "halogen-substituted radicals", for example haloalkyl, are understood to mean radicals halogenated once or more than once up to the maximum possible number of substituents. In the case of polyhalogenation, the halogen atoms may be the same or different. Halogen represents fluorine, chlorine, bromine or iodine, especially fluorine, chlorine or bromine.

The term "alkoxy", either alone or in combination with further terms, for example haloalkoxy, is understood in the present context to mean an O-alkyl radical, where the term "alkyl" is as defined above.

Optionally substituted radicals may be mono- or polysubstituted, where the substituents may be the same or different in the case of polysubstitution.

The 2,2-difluoroethylimine derivatives of the general formula (IV) can be hydrogenated to the corresponding amines of the general formula (III) with reducing agents known per se to those skilled in the art. For example, it is possible to perform the reduction with
complex hydrides,
non-complex metal or semimetal hydrides,
Na/EtOH, or
by catalytic hydrogenation.

Complex hydrides are generally understood to mean metal complexes which contain at least one hydride ligand. Examples thereof are lithium aluminum hydride (LiAlH$_4$), LiAlH(O-tert-butyl)$_3$, LiAlH(O-methyl)$_3$, NaAl(methoxyethoxy)$_2$H (Red-Al, Vitride), NaAlEt$_2$H$_2$, sodium borohydride (NaBH$_4$) and the like. Examples of non-complex metal and semimetal hydrides are AlH$_3$, DIBAL-H (AlH(isobutyl)$_2$) and the like. Among these, the use of sodium borohydride (NaBH$_4$) is particularly preferred. The reaction with the complex metal hydrides or the non-complex metal or semimetal hydrides can be carried out under reduced pressure, at standard pressure or under elevated pressure and at temperatures of –30, to 150° C., preferably –10, to 60° C.

When a catalytic hydrogenation is employed to reduce the compound of the general formula (IV), the catalyst used may be any desired hydrogenation catalyst. Suitable catalysts optionally contain one or more metals of groups 8-10, of the Periodic Table on any desired customary inorganic support. Useful catalysts include, for example, noble metal catalysts, such as ruthenium catalysts, palladium catalysts, platinum catalysts and rhodium catalysts, Raney nickel catalysts and Lindlar catalysts. As well as these heterogeneous catalysts, it is also possible, however, to carrying out hydrogenations over homogeneous catalysts, for example over the Wilkinson catalyst. The corresponding catalysts can also be used in supported form, for example applied to carbon (unactivated or activated carbon), aluminum oxide, silicon dioxide, zirconium dioxide or titanium dioxide. Corresponding catalysts are known per se to those skilled in the art. Raney nickel catalysts are especially preferred.

The catalytic hydrogenation can be carried out under elevated pressure in an autoclave or at standard pressure in a hydrogen gas atmosphere. The hydrogen gas atmosphere may additionally also comprise inert gases, for example argon or nitrogen. The catalytic hydrogenation is preferably carried out at a temperature of 10, to 200° C., more preferably at 10, to 150° C., most preferably at 10 to 60° C. The hydrogen pressure is typically 0.1, to 50, bar, preferably 0.1, to 30, bar.

Further reagents and hydrogenation conditions used for the hydrogenation of imines are described in the publications of Harada, in Patai, "The chemistry of the Carbon-Nitrogen Double Bond", pages 276, to 293;, and of Rylander, "Catalytic Hydrogenation over Platinum Metals", pages 291, to 303, Academic Press, New York, 1967.

In general, it is advantageous to perform the process according to the invention for hydrogenation imines in the presence of solvents (diluents). Solvents are advantageously used in such an amount that the reaction mixture remains efficiently stirrable over the entire process of reduction. Useful solvents for performing the process according to the invention include all organic solvents which are inert under the reaction conditions, the type of solvent used depending on the way in which the reduction is performed, i.e. more particularly on the type of reducing agent.

Examples include: halohydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, methyl n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether and polyethers of ethylene oxide and/or of propylene oxide; amines such as trimethyl-, triethyl-, tripropyl-, tributylamine, N-methylmorpholine, pyridine, alkylated pyridines and tetramethylenediamine; aliphatic, cycloaliphatic or aromatic hydrocarbons such as pentane, n-hexane, n-heptane, n-octane, nonane and technical hydrocarbons which may be substituted by fluorine and chlorine atoms, such as methylene chloride, dichloromethane, trichloromethane, carbon tetrachloride, fluorobenzene, chlorobenzene or dichlorobenzene; for example so-called white spirits comprising components with boiling points in the range, for example, of 40° C. to 250° C., cymene, petroleum fractions within a boiling range of 70° C. to 190° C., cyclohexane, methylcyclohexane, petroleum ether, ligroin, octane, benzene, toluene, chlorobenzene, bromobenzene, nitrobenzene, xylene; esters such as methyl acetate, ethyl acetate, butyl acetate, isobutyl acetate, and dimethyl carbonate, dibutyl carbonate or ethylene carbonate; and aliphatic alcohols, such as methanol, ethanol, n-propanol and isopropanol and n-butanol.

Among the aforementioned solvents, alcohols, in particular methanol and ethanol, especially methanol, are preferred.

The amounts of solvent used in the inventive reaction can be varied within a wide range. In general, amounts of solvent in the range of 1, to 50, times the amount of solvent, more preferably of 2, to 40, times the amount of solvent, especially of 2, to 30, times the amount of solvent, based in each case on the 2,2-difluoroethylimine of the general formula (IV) used, are used.

Preference is additionally given especially to the combination of sodium borohydride (NaBH$_4$) as the hydrogenating agent with alcohols, especially methanol, as the solvent.

The inventive reaction can be carried out with this system composed of sodium borohydride (NaBH$_4$) and methanol especially as follows: the imine is initially charged in the alcohol and the sodium borohydride is added in portions with cooling. Subsequently, the mixture is stirred at a temperature of 30, to 50° C. and then about 1, to 3, equivalents of water are added, based on the amount of alcohol. This is followed by extraction with an organic solvent in a customary manner The hydrogenation is generally effected under those reaction conditions (pressure, temperature, stoichiometry etc.), under which the imine group is hydrogenated to a saturated group, but the other functional groups present in the molecule simultaneously remain unchanged.

The workup (purification) and isolation of the hydrogenated imines can be effected, for example, by crystallization and/or distillation.

The present invention additionally also relates to the use of the compounds of the general formula (IV) to prepare compounds of the general formula (III), as disclosed in the process described above.

The present invention also provides a process for preparing the compounds of the general formula (IV) required for the inventive reaction of the general formula (VI)

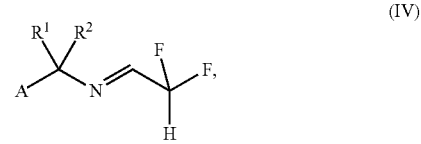
(IV)

in which

A, $R^1$, and $R^2$, are as defined above, where amines

(VI)

are reacted with 2,2-difluoroacetaldehyde (VIIa) or a derivative thereof of the formula (VIIb), (VIIc), (VIId), (VIIe) or (VIIf)

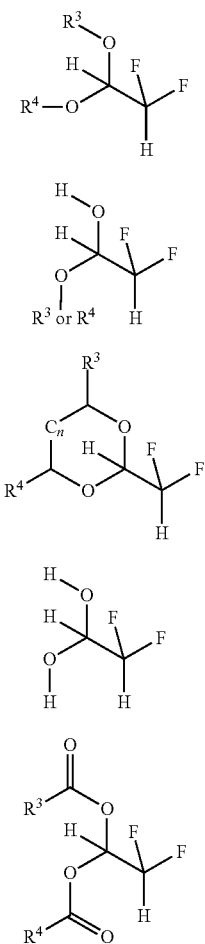

VIIb

VIIc

VIId

VIIe

VIIf where $R^3$, and $R^4$, are each independently H or $C_1$-$C_6$-alkyl and n is 0, 1, or 2, with condensation to give a compound of the general formula (IV).

The 2,2-difluoroacetaldehyde (VIIa) and the 2,2-difluoroacetaldehyde hemiacetal (VIIc) required for this reaction are commercially available and can be prepared by literature methods (Journal of Org. Chem. 58, (1993), 2302;, Synthesis (2007), 1624;, J. Chemical Research (2001)844; Proceedings of the Indian Academy of Science 64;, (1954/55), 108-110;, Bull. Soc. Chim. Belges (1959), 401). The 2,2-difluoroacetaldehyde acetal (VIIb) is described in Journal of Fluorine Chem. 5, (1975), 521-530. The 2,2-difluoroacetaldehyde hydrate (Vile) and the 2,2-difluoroacetaldehyde diacetate (VIIf) are described in Proceedings of the Indian Academy of Science 64;, (1954/55), 108-110.

It is optionally possible to add an acid as a catalyst to the reaction to obtain the compounds of the general formula (IV). Examples thereof are acetic acid, p-toluenesulphonic acid and trifluoroacetic acid. Preference is given to using acetic acid. Acidic salts can also be used, e.g. $KHSO_4$, or $NaHSO_4$.

When catalysts of this kind are used, the amount thereof may be 0.01, to 10, per cent by weight, based on the 2,2-difluoroethylamine used.

In a preferred embodiment of the present invention, 2,2-difluoroacetaldehyde (VIIa) or difluoroacetaldehyde ethyl hemiacetal (VIIc) is used. The reaction to prepare the compounds of the general formula (IV) can additionally also be carried out in such a way that the water formed in the reaction between amine and aldehyde is removed from the reaction mixture by condensation. This is possible, for example, through use of water-binding agents, for example sodium sulphate, magnesium sulphate or molecular sieve, or through use of an apparatus for water separation.

The reaction to prepare the compounds of the general formula (IV) can generally be carried out under reduced pressure, at standard pressure or under elevated pressure. The temperatures employed can likewise vary depending on the substrates used, and are easy for the person skilled in the art to determine by routine tests. For example, the reaction to prepare the compounds of the general formula (IV) can be carried out at a temperature of −20, to 200° C., preferably 10, to 100° C. Particular preference is given to performing the reaction at standard pressure and temperatures of 10, to 100° C.

The reaction to prepare the imines of the general formula (IV) can additionally also be carried out in the presence of solvents (diluents). In this process step too, the solvents are preferably used in such an amount that the reaction mixture remains efficiently stirrable over the entire process of the reduction. Useful solvents for performing the process according to the invention for preparing the 2,2-difluoroethylimine derivatives of the general formula (IV) include all organic solvents which are inert under the reaction conditions.

Examples include: halohydrocarbons, especially chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols, such as methanol, ethanol, isopropanol, butanol; ethers, such as ethyl propyl ether, methyl tert-butyl ether, methyl n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, dioxane, dichlorodiethyl ether and polyethers of ethylene oxide and/or of propylene oxide; nitrohydrocarbons such as nitromethane, nitroethane, nitropropane, nitrobenzene, chloronitrobenzene, o-nitrotoluene; nitriles such as acetonitrile, methyl nitrile, propionitrile, butyronitrile, isobutyronitrile, benzonitrile, phenyl nitrile, m-chlorobenzonitrile, and compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide, diisoamyl sulphoxide; sulphones such as dimethyl sulphone, diethyl sulphone, dipropyl sulphone, dibutyl sulphone, diphenyl sulphone, dihexyl sulphone, methyl ethyl sulphone, ethyl propyl sulphone, ethyl isobutyl sulphone and pentamethylene sulphone; aliphatic, cycloaliphatic or aromatic hydrocarbons such as pentane, hexane, heptane, octane, nonane and technical hydrocarbons which may be substituted by fluorine and chlorine atoms, such as methylene chloride, dichloromethane, trichloromethane, carbon tetrachloride, fluorobenzene, chlorobenzene or dichlorobenzene; for example so-called white spirits comprising components with boiling points in the range, for example, of 40° C. to 250° C., cymene, petroleum fractions within a boiling range of 70° C. to 190° C., cyclohexane, methylcyclohexane, petroleum ether, ligroin, octane, benzene, toluene, chlorobenzene, bromobenzene, nitrobenzene and xylene. Among the aforementioned solvents, xylene, chlorobenzene, cyclohexane and toluene are especially preferred.

In a further embodiment, the reaction between amine and aldehyde can also be effected in substance.

If the reaction is carried out in a solvent, the solvent can be removed by distillation after the end of the reaction. This can be done under standard pressure or reduced pressure, at room temperature or elevated temperatures. The mixture can also be transferred directly into the hydrogenation, which is advantageous especially owing to economic considerations. In this embodiment of the process according to the invention, a workup of the 2,2-difluoroethylimine derivative is then dispensed with.

The present invention also provides a process for preparing compounds of the formula (III) by hydrogenating compounds of the formula (IV), wherein the compounds of the general formula (IV) obtained by the above-described process are used as starting compounds.

The present invention further additionally provides compounds of the general formula (IV), which are used as intermediates in the preparation of the target compounds of the general formula (III):

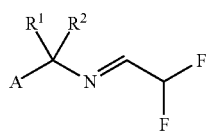

(IV)

in which the A radical is pyrid-2-yl or pyrid-4-yl, or pyrid-3-yl which is optionally 6-substituted by fluorine, chlorine, bromine, methyl, trifluoromethyl or trifluoromethoxy, or pyridazin-3-yl which is optionally 6-substituted by chlorine or methyl, or pyrazin-3-yl, or 2-chloropyrazin-5-yl, or 1,3-thiazol-5-yl which is optionally 2-substituted by chlorine or methyl, or is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, $C_1$-$C_4$-alkyl (which is optionally substituted by fluorine and/or chlorine), $C_1$-$C_3$-alkylthio (which is optionally substituted by fluorine and/or chlorine), or $C_1$-$C_3$-alkylsulphonyl (which is optionally substituted by fluorine and/or chlorine), or is

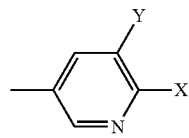

in which

X is halogen, alkyl or haloalkyl and

Y is halogen, alkyl, haloalkyl, haloalkoxy, azido or cyano.

$R^1$, and $R^2$, are each independently hydrogen or $C_1$-$C_6$-alkyl.

Preferred, particularly preferred and very particularly preferred substituents or ranges of the A radical shown in the abovementioned general formulae (III) and (IV) are elucidated below.

A is preferably selected from the group consisting of 6-fluoropyrid-3-yl, 6-chloropyrid-3-yl, 6-bromopyrid-3-yl, 6-methylpyrid-3-yl, 6-trifluoromethylpyrid-3-yl, 6-trifluoromethoxypyrid-3-yl, 6-chloro-1,4-pyridazin-3-yl, 6-methyl-1,4-pyridazin-3-yl, 2-chloro-1,3-thiazol-5-yl or 2-methyl-1,3-thiazol-5-yl, 2-chloropyrimidin-5-yl, 2-trifluoromethylpyrimidin-5-yl, 5,6-difluoropyrid-3-yl, 5-chloro-6-fluoropyrid-3-yl, 5-bromo-6-fluoropyrid-3-yl, 5-iodo-6-fluoropyrid-3-yl, 5-fluoro-6-chloropyrid-3-yl, 5,6-dichloropyrid-3-yl, 5-bromo-6-chloropyrid-3-yl, 5-iodo-6-chloropyrid-3-yl, 5-fluoro-6-bromopyrid-3-yl, 5-chloro-6-bromopyrid-3-yl, 5,6-dibromopyrid-3-yl, 5-fluoro-6-iodopyrid-3-yl, 5-chloro-6-iodopyrid-3-yl, 5-bromo-6-iodopyrid-3-yl, 5-methyl-6-fluoropyrid-3-yl, 5-methyl-6-chloropyrid-3-yl, 5-methyl-6-bromopyrid-3-yl, 5-methyl-6-iodopyrid-3-yl, 5-difluoromethyl-6-fluoropyrid-3-yl, 5-difluoromethyl-6-chloropyrid-3-yl, 5-difluoromethyl-6-bromopyrid-3-yl and 5-difluoromethyl-6-iodopyrid-3-yl.

A is more preferably selected from the group consisting of 6-fluoropyrid-3-yl, 6-chloropyrid-3-yl, 6-bromopyrid-3-yl, 6-chloro-1,4-pyridazin-3-yl, 2-chloro-1,3-thiazol-5-yl, 2-chloropyrimidin-5-yl, 5-fluoro-6-chloropyrid-3-yl, 5,6-dichloropyrid-3-yl, 5-bromo-6-chloropyrid-3-yl, 5-fluoro-6-bromopyrid-3-yl, 5-chloro-6-bromopyrid-3-yl, 5,6-dibromopyrid-3-yl, 5-methyl-6-chloropyrid-3-yl, 5-chloro-6-iodopyrid-3-yl and 5-difluoromethyl-6-chloropyrid-3-yl.

A is most preferably selected from the group consisting of 6-chloropyrid-3-yl, 6-bromopyrid-3-yl, 6-chloro-1,4-pyridazin-3-yl, 2-chloro-1,3-thiazol-5-yl, 5-fluoro-6-chloropyrid-3-yl and 5-fluoro-6-bromopyrid-3-yl.

$R^1$, and $R^2$, are more preferably hydrogen or $C_1$-$C_3$, alkyl. $R^1$, and $R^2$, are most preferably hydrogen.

The present invention also provides for the use of the compounds of the general formula (IV) as reactants to prepare 2,2-difluoroethylamine derivatives of the general formula (III).

Proceeding from the compounds of the general formula (III) which are obtained by the process according to the invention, it is possible to prepare insecticidally active enaminocarbonyl compounds which include 2,2-difluoroethylamino units and are described, for example, in international patent applications WO 2007/115644, and WO 2007/115646.

For this purpose, the compounds of the general formula (III)

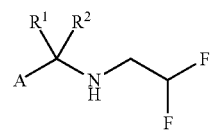

(III)

where $R^1$, and $R^2$, are each as defined above can be alkenylated on the secondary amine nitrogen, for example by reaction with tetronic acid or derivatives thereof. A corresponding reaction is described in detail in scheme I of WO 2007/115644, and leads directly to the insecticidally active enaminocarbonyl compounds.

The present invention is illustrated in detail by the examples which follow, though the examples should not be interpreted in such a manner as to limit the invention.

PREPARATION EXAMPLES

Example 1

1-(6-Chloropyridin-3-yl)-N-[(1E)-2,2-difluoroethylidene]methanamine

To a solution of 63.73, g of 6-chloro-3-aminomethylpyridine in 41, g of toluene were added 35.4, g of 2,2-difluoroacetaldehyde at room temperature. After addition of the 2,2-difluoroacetaldehyde, the initial suspension became a clear solution over the course of 20, min. The reaction mixture was stirred at room temperature for 2, hours. Subsequently, 106, g of anhydrous magnesium sulphate were added and the mixture was stirred at 50° C. for a further 5, hours. The reaction mixture was cooled to room temperature and filtered, and the filter residue was washed with toluene. The solvent was removed under reduced pressure and the oily residue was distilled at 4, mbar. This gave 85.3, g of 1-(6-chloropyridin-3-yl)-N-[(1E)-2,2-difluoroethylidene]methanamine 99.5% (this corresponds to 93.8% yield).

$^1$H NMR (CDCl$_3$, 298K) δ: 4.7, s (2H), 5.9-6.2, t (1 H, C$\underline{H}$F$_2$), 7.43, d (1H), 7.6, d (1H), 7.7, d (1H), 8.3, s(1H)

Example 2

N-[(6-Chloropyridin-3-yl)methyl)]-2,2-difluoroethylamine

To a solution of 80, g of 1-(6-chloropyridin-3-yl)-N-[(1E)-2,2-difluoroethylidene]methanamine (from Example 1) in 343, g of ethanol were added 5, g of Raney nickel catalyst, and hydrogenation was effected with 20, bar of hydrogen at room temperature for 24, h. The catalyst was filtered off, the residue was washed with 100, ml of ethanol and the solvent was removed under reduced pressure. This gave 78.8, g of N-[(6-chloropyridin-3-yl)methyl)]-2,2-difluoroethylamine in a purity of 99% (this corresponds to 96.7% yield).

NMR (d-DMSO): 1H (s, 8.35, ppm); 1H (dd, 7.8, ppm); 1H (d, 7.46, ppm); 1H (tt, 6.02, ppm); 2H (s, 3.8, ppm); 2H (td, 2.9, ppm)

Example 3

N-[(6-Chloropyridin-3-yl)methyl)]-2,2-difluoroethylamine

To a solution of 5, g of 1-[(6-chloropyridin-3-yl)-N-[(1E)-2,2-difluorethylidene]methanamine in 23, g of ethanol were added 1.1, g of sodium borohydride in portions, and the mixture was stirred at room temperature. Subsequently, the mixture was heated briefly to 50° C. and then poured onto 100 ml of water. The mixture was extracted twice with 100, ml each time of methylene chloride and the combined organic phases were concentrated under reduced pressure. This gave 4.5, g of N-[(6-chloropyridin-3-yl)methyl)]-2,2-difluoroethylamine in a purity of 93% (this corresponds to 86% yield).

NMR data: see Example 2

The invention claimed is:
1. A process for preparing 2,2-difluoroethylamine derivatives, comprising hydrogenating 2,2-difluoroethylimine derivatives of formula (IV) to a corresponding 2,2-difluoroethylamine derivative of formula (III):

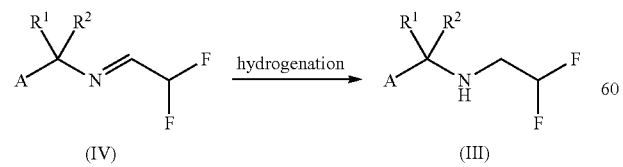

where the A radical in formulae (III) and (IV) is:
pyrid-2-yl or pyrid-4-yl, or pyrid-3-yl which is optionally 6-substituted by fluorine, chlorine, bromine, methyl, trifluoromethyl or trifluoromethoxy, or pyridazin-3-yl which is optionally 6-substituted by chlorine or methyl, or pyrazin-3-yl, or 2-chloropyrazin-5-yl, or 1,3-thiazol-5-yl which is optionally 2-substituted by chlorine or methyl, or is pyrimidinyl, pyrazolyl, thiophenyl, oxazolyl, isoxazolyl, 1,2,4-oxadiazolyl, isothiazolyl, 1,2,4-triazolyl or 1,2,5-thiadiazolyl, which is optionally substituted by fluorine, chlorine, bromine, cyano, nitro, $C_1$-$C_4$-alkyl, which is optionally substituted by fluorine and/or chlorine, $C_1$-$C_3$-alkylthio, which is optionally substituted by fluorine and/or chlorine, or $C_1$-$C_3$-alkylsulphonyl, which is optionally substituted by fluorine and/or chlorine, or is

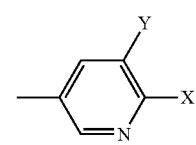

in which
X is halogen, alkyl or haloalkyl and
Y is halogen, alkyl, haloalkyl, haloalkoxy, azido or cyano, and $R^1$ and $R^2$ are each independently H or $C_1$-$C_6$-alkyl.

2. The process according to claim 1, wherein the hydrogenation is carried out with complex hydrides, non-complex metal or semimetal hydrides, Na/EtOH and/or by catalytic hydrogenation.

3. A process according to claim 1, wherein the compound of formula (IV) is prepared by reacting
an amine of formula (VI)

with 2,2-difluoroacetaldehyde (VIIa) or a derivative thereof of formula (VIIb), (VIIc), (VIId), (VIIe) or (VIIf)

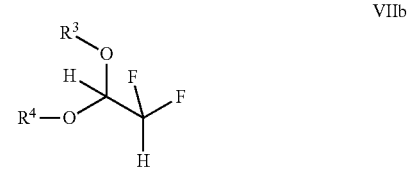

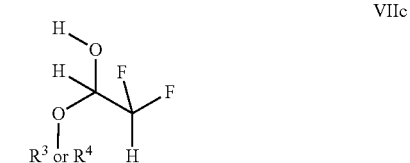

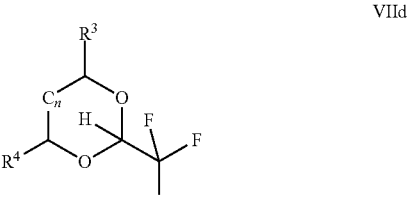

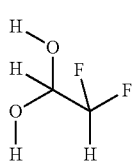
VIIe
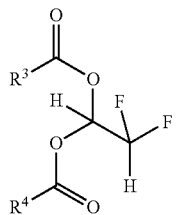
VIIf
where $R^3$ and $R^4$ are each independently H or $C_1$-$C_6$-alkyl and n is 0, 1 or 2, with condensation to give a compound of formula (IV).
* * * * *